(12) United States Patent
Leonard et al.

(10) Patent No.: US 7,319,518 B2
(45) Date of Patent: Jan. 15, 2008

(54) DOUBLE SIDE POLISHED WAFER SCRATCH INSPECTION TOOL

(75) Inventors: Robert Tyler Leonard, Raleigh, NC (US); Jason Ronald Jenny, Wake Forest, NC (US)

(73) Assignee: Cree, Inc., Durham, NC (US)

( * ) Notice: Subject to any disclaimer, the term of this patent is extended or adjusted under 35 U.S.C. 154(b) by 219 days.

(21) Appl. No.: 11/211,061

(22) Filed: Aug. 24, 2005

(65) Prior Publication Data

US 2007/0081150 A1    Apr. 12, 2007

(51) Int. Cl.
*G01N 21/00* (2006.01)

(52) U.S. Cl. .................................... 356/237.2

(58) Field of Classification Search ............ None
See application file for complete search history.

(56) References Cited

U.S. PATENT DOCUMENTS

| | | | |
|---|---|---|---|
| 4,449,818 A | | 5/1984 | Yamaguchi et al. |
| 4,626,101 A | | 12/1986 | Ogawa et al. |
| 4,652,757 A | | 3/1987 | Carver |
| 4,893,932 A | | 1/1990 | Knollenberg |
| 4,957,368 A | | 9/1990 | Smith |
| 5,032,734 A | * | 7/1991 | Orazio et al. .......... 250/559.46 |
| 5,424,536 A | | 6/1995 | Moriya |
| 5,465,145 A | | 11/1995 | Nakashige et al. |
| 5,518,576 A | | 5/1996 | Mendelovich et al. |
| 5,818,576 A | | 10/1998 | Morishige et al. |
| 6,034,776 A | | 3/2000 | Germer et al. |
| 6,169,601 B1 | | 1/2001 | Eremin et al. |
| 6,271,961 B1 | | 8/2001 | Emery et al. |
| 6,528,333 B1 | | 3/2003 | Jun et al. |
| 6,552,778 B1 | | 4/2003 | Konagaya |

OTHER PUBLICATIONS

Jacques I. Pankove; Optical Processes in Semiconductors, pp. 34-37, Dover Publications, Inc. New York, no date.

\* cited by examiner

*Primary Examiner*—Tu T Nguyen
(74) *Attorney, Agent, or Firm*—Summa, Allan & Addition, P.A.

(57) ABSTRACT

The invention is a method of inspecting a semiconductor wafer surface for scratches. The method includes positioning a semiconductor wafer for illumination by a radiation source and adjacent a background material that will absorb radiation from the radiation source, directing radiation at a surface of the wafer from the radiation source that has a wavelength that will be absorbed by the fundamental absorption of the wafer, filtering or otherwise limiting the radiation to allow only radiation having wavelengths that are absorbed by the fundamental absorption of the wafer to pass, and detecting radiation scattered on the surface of the wafer and filtered, by position, to thereby identify the location of the scratches on the surface of the wafer, while the absorption of the background material prevents other radiation from the source from interfering with the detection of the scratch-scattered radiation.

51 Claims, 1 Drawing Sheet

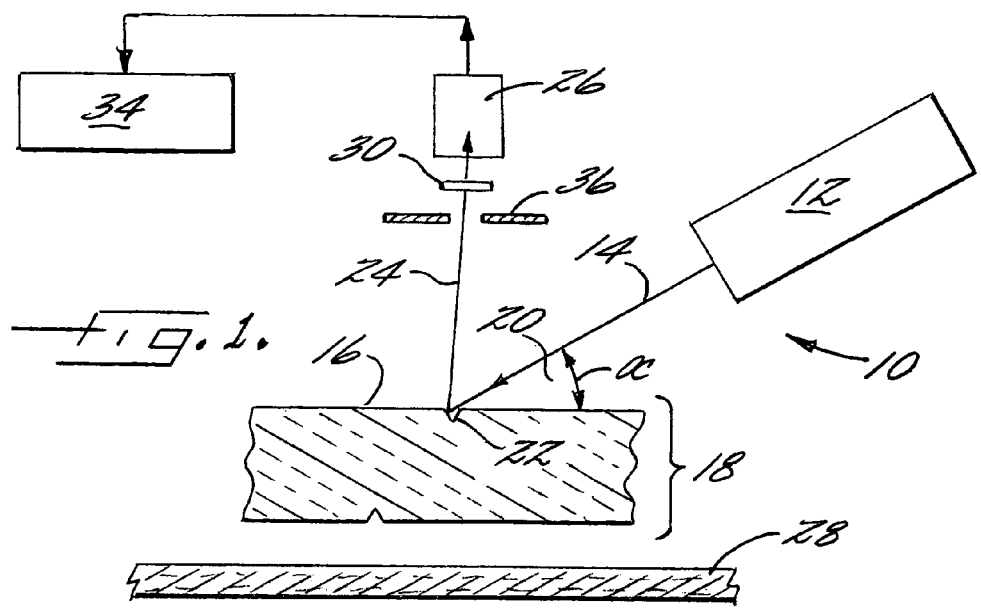
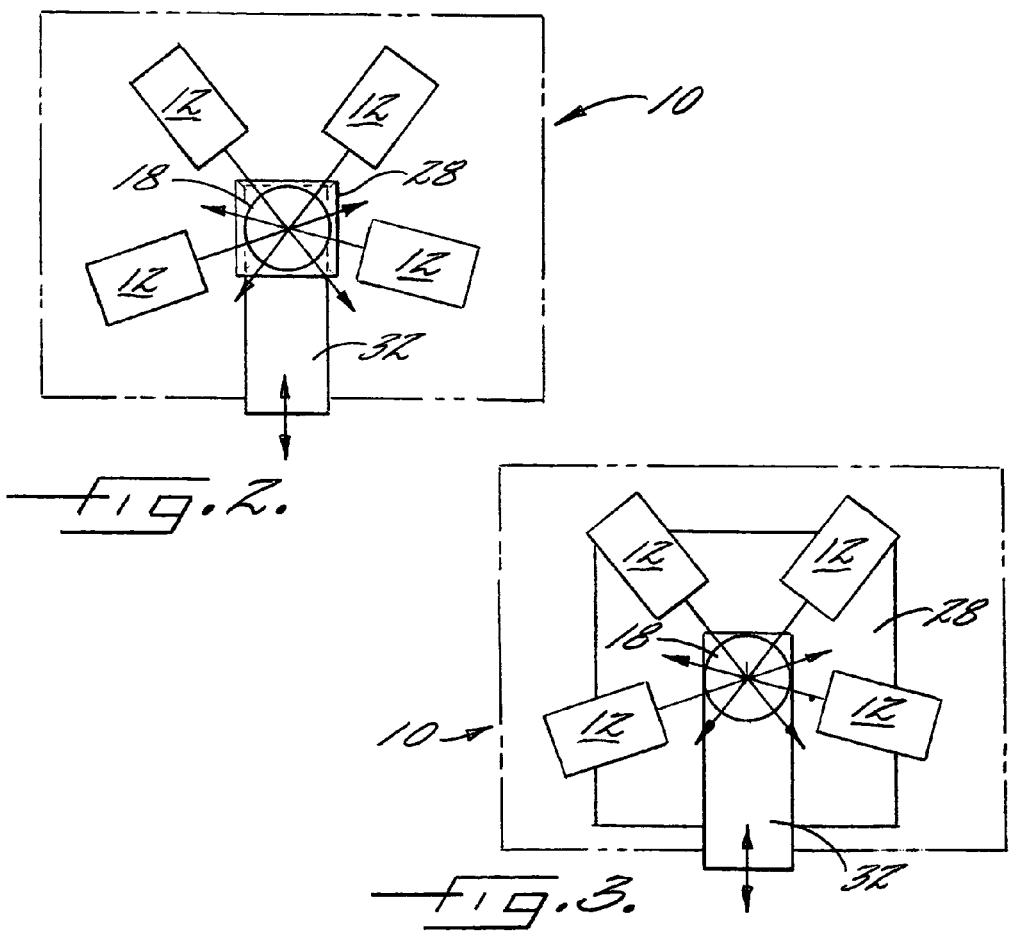

DOUBLE SIDE POLISHED WAFER SCRATCH INSPECTION TOOL

BACKGROUND OF THE INVENTION

The present invention relates to a method and apparatus for detecting scratches on the surface of a semiconductor wafer. In particular, the invention relates to detecting surface scratches on high quality, transparent, single crystal silicon carbide wafers that are polished on both sides.

Silicon carbide has found use as semiconductor material for various electronic devices and purposes in recent years. Silicon carbide is especially useful due to its physical strength and high resistance to chemical attack. Silicon carbide also has excellent electronic properties, including radiation hardness, high breakdown field, a relatively wide band gap, high saturated electron drift velocity, and high-temperature stability.

Single crystal silicon carbide is often produced by a seeded sublimation growth process. In a typical silicon carbide growth technique, the seed crystal and a source powder are both placed in a reaction crucible which is heated to the sublimation temperature of the source and in a manner that produces a thermal gradient between the source and the marginally cooler seed crystal. The thermal gradient encourages vapor phase movement of the materials from the source to the seed followed by condensation upon the seed and the resulting bulk crystal growth. The method is also referred to as physical vapor transport (PVT).

The bulk single crystal of silicon carbide may then be desirably cut into wafers and polished prior to the growth of epitaxial layers and the formation of devices on the wafers. Common techniques for polishing silicon carbide wafers sometimes scratch the wafer surface. The location, size, and depth of these scratches are best identified early before they become problematic. The quality of the growth surface affects the quality of any deposited epitaxial layers, which in turn affects the quality of any resulting devices formed in or from the SiC and the epilayers.

In some conventional techniques, a skilled person visually inspects a wafer to locate scratches, attempting to identify scratches by holding the wafer up to the light. The inspection identifies the side of the wafer containing scratches allowing quality control for the side used for semiconductor device preparation. This technique suffers several drawbacks, including frequent inaccuracy, subjectivity, and potentially the need for persons to touch the wafer surfaces.

Other scratch detection techniques offer more precision by directing light at the wafer surface, and then measuring (using some sort of detector) the light as reflected or scattered from the wafer surface to identify various flaws.

High quality single crystal silicon carbide is often (and intentionally) transparent in the visible frequencies, as well as some of the UV frequencies. Thus, light in the visible wavelengths fails to discriminate between flaws (scratches) on the growth surface and flaws on the opposite surface. This problem is exacerbated in "double-side polished" wafers; i.e. those that have been sliced from boules and polished on both faces.

If the scratch remains undetected until after production of a device on the wafer surface, then costly reworks and repolishing steps must be undertaken to correct this mistake. Such reworking does not, however, address the detection problem and thus does not guarantee that the same mistake will not be repeated.

Efficient techniques for accurately identifying the presence of scratches on a semiconductor wafer surface prior to device preparation are therefore needed, including techniques capable of successfully identifying scratches on transparent double-side polished wafers.

SUMMARY

In one aspect, the present invention is an efficient technique for accurately identifying the presence of scratches on a semiconductor wafer surface prior to device preparation.

In another aspect, the invention is a method of inspecting a semiconductor wafer surface for scratches. The method includes positioning a semiconductor wafer for illumination by a radiation source and adjacent a background material that will absorb radiation from the radiation source, directing radiation from the radiation source that has wavelengths that will be absorbed within the wafer by the fundamental absorption of the wafer, filtering (or otherwise limiting) the radiation to allow only radiation having the same wavelengths as the wavelengths that are absorbed by the fundamental absorption of the wafer to pass, and detecting radiation scattered on the surface of the wafer and filtered, by position, to thereby identify the location of the scratches on the surface of the wafer, while the absorption of the background material prevents other radiation from the source from interfering with the detection of the scratch-scattered radiation.

In yet another aspect, the invention is a method of inspecting a surface of a double side polished silicon carbide semiconductor wafer for scratches. The method includes positioning a double side polished silicon carbide semiconductor wafer for illumination by a radiation source and adjacent a UV-absorbing material that will absorb radiation from the radiation source, directing UV-radiation at a first surface of the polished wafer from the radiation source that has at least a wavelength that will be absorbed by the fundamental absorption of silicon carbide, filtering UV-radiation having a wavelength that would not be absorbed by the fundamental absorption of the SiC wafer and allow radiation having a wavelength that would be absorbed by the fundamental absorption of the SiC wafer to pass, and detecting radiation scattered by scratches on the surface of the SiC wafer and filtered to determine the location of scratches on the surface of the SiC wafer.

In another aspect, the invention is an apparatus for detecting scratches on a surface of a semiconductor wafer. The apparatus includes at least one radiation source positioned for directing radiation at the surface of a semiconductor wafer to be inspected, directing the radiation at an angle at which scratches in the wafer surface will scatter the directed radiation, a radiation detector positioned to detect source-generated and scratch-scattered radiation from the surface of the wafer, a background material positioned relative to said source and said detector for absorbing radiation from the source that is neither absorbed by the wafer nor scattered by the wafer surface to thereby help prevent non-scratch scattered light from reaching the detector, and at least one filter positioned relative to said wafer and said detector for absorbing radiation having a wavelength that would not be absorbed by the fundamental absorption of the wafer while allowing radiation having a wavelength that would be absorbed by the fundamental absorption of the wafer to pass.

The foregoing and other objects and advantages of the invention and the manner in which the same are accomplished will become clearer based on the following detailed description taken in conjunction with the following drawings.

BRIEF DESCRIPTION OF THE DRAWINGS

FIG. 1 is a cross sectional schematic representation of an apparatus in accordance with the present invention;

FIG. 2 is a schematic representation of a portion of an apparatus having multiple radiation sources in accordance with the present invention; and FIG. 3 is a schematic representation of a portion of an alternative embodiment of an apparatus having multiple radiation sources in accordance with the present invention.

DETAILED DESCRIPTION

The present invention relates to a method and apparatus for detecting scratches on the surface of a semiconductor wafer. In particular, the invention relates to detecting surface scratches on high quality, transparent, double-side polished single crystal silicon carbide wafers.

For purposes of clarity, the terms "illuminate" and "illuminated" as used herein encompass illumination by visible light and radiation by UV-radiation. Additionally, the terms "radiation" and "light" will be used interchangeably. The terms "UV-radiation" and "visible light" are used herein in accordance with their accepted definitions in the art. Those of ordinary skill in the art will recognize that the descriptions given herein are most appropriately given in a general and schematic sense with the recognition that those persons of skill in this art will be able to carry out the improvements of the invention based on the disclosures herein without undue experimentation.

The invention is discussed with reference to 4H silicon carbide substrates for ease of discussion. Those of ordinary skill in the art will recognize, however, that the method and apparatus of the invention are applicable to SiC wafers of other polytypes, as well as wafers formed of substances other than SiC. The disclosure, figures, and claims should be construed to include these variations.

The invention uses the relationship between the bandgap of SiC (2.98 eV for the 6H and 3.2 eV for the 4H polytypes) to address the transparency problem referred to in the background. By limiting the radiation (as generated by the source, or as detected by the detector, or as filtered between the source and the detector) to wavelengths (frequencies) near the SiC bandgap, the invention encourages any non-scratch-scattered light to be absorbed in the crystal by the fundamental absorption of the crystal, or filtered from being considered, or not generated, or not detected, or any combination of these techniques.

As will be recognized by those having ordinary skill in the art, the fundamental absorption of a crystal occurs at a wavelength where a photon is absorbed and an electron is excited from an occupied valence band state to an unoccupied conduction band state. The excited electron then returns to the valence band by various transitions, either direct or indirect in a way to conserve energy (e.g. by creating heat, emitting another photon, or both).

In one embodiment, as depicted in FIG. 1, the invention is an apparatus 10 for detecting scratches on a surface of a semiconductor wafer. A radiation source 12 is positioned for directing radiation 14 at the surface 16 of a semiconductor wafer 18 to be inspected. The radiation source 12 is positioned at an angle 20 (usually other than normal to the wafer surface) at which scratches 22 in the wafer surface 16 will tend to scatter the directed radiation 24. A radiation detector 26 is positioned to detect source-generated and scratch-scattered radiation 24 from the surface of the wafer 16. The apparatus further includes a background material 28 positioned relative to the radiation source 12 and the detector 26 for absorbing radiation from the source that is neither absorbed by the wafer 16 nor scattered by scratches 22 on the wafer surface 16 to thereby help prevent non-scratch scattered light from reaching the detector 26, and a filter 30 positioned relative to the wafer 18 and the detector 26 for absorbing radiation having a wavelength that would not be absorbed by the fundamental absorption of the wafer 18 while allowing radiation having a wavelength that would be absorbed by the fundamental absorption of the wafer 18 to pass through the filter 30.

Accordingly, a suitable background material will be selected to favorably absorb the radiation produced by the source (or by the filter, if the filter is used at the source rather than at the detector). For example, UV absorbing glass is well-understood and widely available. Thus, those of skill in this art will be able to select the background material without undue experimentation.

Single (or narrow) wavelength UV sources, although available, (e.g. UV lasers) are generally complex and less commercially suitable for an inspection tool of this nature. Similarly, detectors limited to narrow or single wavelengths are likewise unavailable or less practical or less commercially available or attractive. Accordingly, the invention usually takes advantage of filters and a radiation-absorbing background to limit the scattered and detected wavelengths. The more complex systems, however, certainly fall within the scope of the invention and the claims.

In some embodiments, as depicted in FIGS. 2 and 3, the apparatus may optionally include a platform 32 positioned to hold a semiconductor wafer 18 in the proper orientation for inspection. The platform 32 may be a slide that allows the wafer 18 to be inserted and removed from the apparatus 10. Alternatively, the platform 32 may be a conveyer that allows sequential analysis of more than one wafer or a rotating platform that is capable of sequentially positioning more than one wafer for inspection. The platform 32 may also include means for rotating the platform to more fully illuminate the wafer surface 16 from different positions relative to the position of the radiation source 12.

Where a platform 32 is included in the apparatus 10, the background material 28 may be in the form of a UV-absorbing coating layer on the platform 32. Alternatively, the background material 28 may be situated between the platform 32 and the semiconductor wafer 18 as depicted in FIG. 2 or, as depicted in FIG. 3, where the platform 32 is situated above the background material 28, the wafer 18 may be placed in a hole in the platform 32.

Appropriate UV detectors are commercially available and well-understood. For the imaging aspects of the invention a charge coupled display (CCD) camera that is sensitive to UV radiation (either from its photosensors or from filtering or converting the scattered UV light) is a useful and appropriate detector.

In another embodiment, a plurality of radiation source positions may be employed to more completely illuminate scratches 22 of different orientations on the wafer surface 16. The plurality of radiation source positions may be achieved by moving a single radiation source 12 to a plurality of positions in the apparatus 10. Alternatively, and as depicted in FIGS. 2 and 3, the plurality of radiation source positions may be achieved by including more than one radiation source 12 in the apparatus. A sufficient number of radiation sources 12 should be included to completely illuminate scratches 22 of different orientations on the wafer surface 16. The radiation source (or sources) is preferably a UV-radiation source, a visible light source, or a combination UV/visible source.

In many embodiments the apparatus includes at least one filter positioned relative to the wafer and the detector for absorbing radiation having wavelengths other than those absorbed by the fundamental absorption of the wafer, while allowing wavelengths that would be absorbed by the fundamental absorption of the wafer to pass. The filter is preferably positioned between the wafer and the detector, and filters the scratch-scattered light. Alternatively, the filter may be positioned between the source and the wafer to filter out the radiation that would pass through the wafer to the background material, only allowing radiation having wavelengths that would be absorbed by the fundamental absorption of the wafer to pass to the wafer. In a preferred embodiment, radiation having a wavelength of between about 330 and 360 nm is allowed to pass through the filter regardless of the location of the filter.

In some embodiments, the apparatus 10 includes an image capture board for receiving data from the detector 26 and transferring it to (computer) memory for then mapping the surface of the wafer 16. The apparatus 10 may also preferably include a processor to aid in the mapping of the wafer surface 16. Those of skill in the art will recognize that off-the-shelf processors or image-capture boards are suitable for use in accordance with the present invention, enabling one of skill in the art to select an appropriate processor or image capture board without undue experimentation.

It may be preferred to include an aperture 36 between the wafer 18 and the filter 30 to aid in the prevention of saturation of the filter 30 and the detector 26 by preventing stray radiation from reaching the filter 30 and limiting the radiation reaching the filter 30 to scratch-scattered radiation 24.

In another embodiment, the invention is a method of inspecting a semiconductor wafer surface for scratches. The method includes positioning a semiconductor wafer, preferably a polished semiconductor wafer and most preferably a double side polished silicon carbide wafer, for illumination by a radiation source and adjacent a background material that will absorb radiation from the radiation source, directing radiation from the radiation source to the surface of the wafer, preferably radiation that includes wavelengths that will be absorbed by the fundamental absorption of the wafer, and most preferably ultraviolet radiation; filtering the radiation to allow only radiation having wavelengths that would be absorbed by the fundamental absorption of the wafer to pass; and detecting radiation scattered by scratches on the surface and filtered, by position, to thereby identify the location of the scratches on the surface of the wafer, while the absorption by the background material prevents other radiation from the source from interfering with the scratch-scattered radiation. The method may also include mapping the surface of the wafer to identify the exact location of scratches on the wafer surface. Mapping of the surface of the wafer occurs by transmitting the wavelength of the detected scratch-scattered radiation to a processor, an image capture board, or both.

In a preferred embodiment, the method includes positioning a semiconductor wafer thick enough to absorb substantially all of the radiation having a wavelength that is absorbed by the fundamental absorption of the wafer directed at the wafer from the source and to prevent such radiation from the source from passing through the wafer and illuminating the backside of the wafer for illumination by a radiation source and adjacent a background material.

In this regard, the wafer thickness required will be a function of the semiconductor material, the wavelength of the incident radiation, and the intensity of the source. In one embodiment the wafer can be thick enough so that the impinging radiation is extinguished before it ever reaches the back side of the wafer. In another embodiment, the functional thickness is sufficient to extinguish light from the source that could otherwise travel entirely through to the back surface of the wafer and then be reflected to emerge from front (illuminated) surface of the wafer. Such back-reflected light would be detected and improperly interpreted as a scratch. Thus, those persons of ordinary skill in this art will be able to calculate an appropriate thickness for either embodiment based upon the extinction (absorbance) coefficient of the semiconductor material at the relevant wavelength (or wavelengths) and upon the intensity of the source.

The step of directing radiation at the surface of the wafer preferably includes directing the radiation at an angle that will reduce the specular back reflection from the wafer and will increase or enhance the scattering produced by scratches present on the surface of the wafer. Angles other than normal (i.e., 90°) to the wafer surface are better for this purpose, with angles of between about 20° and 40° to the surface of the wafer being more preferred. The step of directing radiation further includes directing radiation that is at least partially outside the visible range. Preferred radiation has a wavelength of between about 300 nm and 400 nm, more preferably between about 330 and 360 nm.

Directing radiation at the surface of the wafer from more than one location improves the illumination of scratches having different orientations on the surface of the wafer. The step of directing radiation from more than one location includes means for moving the radiation source to different locations, directing radiation at the surface from more than one radiation source, and a combination of both techniques. In one alternative, the wafer may be rotated while radiation is directed from one location to illuminate scratches having different orientations on the surface of the wafer.

The step of positioning a wafer adjacent a background material that will absorb wavelengths from the source including the wavelengths that are absorbed in the wafer based on the bandgap of the wafer includes positioning the wafer adjacent a background material that will absorb radiation that is not absorbed by the wafer, as well as stray radiation that does not strike the wafer. Of course, it will be understood that a background that (theoretically) absorbed all wavelengths would be ideal for this purpose and the background need not be limited in its absorbance characteristics.

In another preferred embodiment, a method of inspecting a surface of a polished silicon carbide semiconductor wafer for scratches includes positioning a polished silicon carbide semiconductor wafer for illumination by a radiation source and adjacent a UV-absorbing material that will absorb radiation from the radiation source, directing UV-radiation from the radiation source, preferably UV-radiation having wavelengths that will be absorbed by the fundamental absorption of silicon carbide, at a first surface of the polished wafer, filtering UV-radiation to remove wavelengths that would not be absorbed by the fundamental absorption of the SiC wafer and allow radiation having wavelengths that would be absorbed by the fundamental absorption of the SiC wafer to pass, and detecting radiation scattered by scratches on the surface of the SiC wafer and filtered to determine the location of the scratches on the surface of the silicon carbide wafer. The method may further include mapping the surface of the wafer after the step of filtering the scratch-scattered radiation. Mapping of the surface of the wafer occurs by transmitting the wavelength of the detected scratch-scattered radiation to a processor, an image capture board, or both.

The silicon carbide wafer is preferably thick enough to absorb substantially all of the radiation having a wavelength that will be absorbed by the fundamental absorption of the wafer directed at the wafer from the source and to prevent such radiation from the source from passing through the wafer and illuminating the backside of the wafer. A preferred background material, such as UV-absorbing glass, positioned adjacent the wafer preferably absorbs stray reflection, UV-radiation that is not absorbed by the fundamental absorption of the wafer, and back-reflection, thereby preventing saturation of the detector.

For purposes of scratch detection on transparent SiC crystals, the UV-radiation should have a wavelength of between about 300 nm and 400 nm, and more preferably between about 330 and 360 nm, wavelengths that are most readily absorbed based upon silicon carbide's bandgap. Radiation directed at the surface of the wafer preferably strikes the wafer at an angle that will illuminate scratches present on the surface of the silicon carbide wafer and allow for scattering of the radiation by the scratches, preferably at an angle of between about 20° and 40° to the surface of the wafer.

In the drawings and specification there has been set forth a preferred embodiment of the invention, and although specific terms have been employed, they are used in a generic and descriptive sense only and not for purposes of limitation, the scope of the invention being defined in the claims.

The invention claimed is:

1. A method of inspecting a semiconductor wafer surface for scratches, the method comprising:
    positioning a semiconductor wafer for illumination by a radiation source and adjacent a background material that will absorb radiation from the radiation source that is neither absorbed by the wafer nor scattered by scratches on the wafer surface;
    directing radiation at a surface of the wafer from the radiation source that includes wavelengths that will be absorbed by the fundamental absorption of the semiconductor; and
    identifying the position of scratches on the surface of the wafer by detecting the position of radiation from the source that is limited to wavelengths near the wavelength that will be absorbed by the fundamental absorption and that has been scattered by scratches on the surface of the wafer, while the absorption of the background material prevents other radiation from the source from interfering with the detection of the scratch-scattered radiation.

2. A method according to claim 1 comprising filtering the radiation to allow only radiation having wavelengths near the wavelength that will be absorbed by the fundamental absorption of the wafer to be detected.

3. A method of inspecting a semiconductor wafer surface according to claim 2 wherein the step of filtering radiation comprises filtering radiation at least partially outside of the visible portion of the spectrum and filtering the scattered radiation through a filter that absorbs substantially all visible light.

4. A method of inspecting a semiconductor wafer surface for scratches according to claim 2 wherein the step of filtering the radiation comprises filtering the scratch-scattered radiation.

5. A method of inspecting a semiconductor wafer surface for scratches according to claim 2 wherein the step of filtering the radiation comprises filtering the radiation from the source before it reaches the wafer surface.

6. A method of inspecting a semiconductor wafer surface according to claim 2 wherein the step of detecting the filtered radiation to determine the location of the scratches on the surface of the wafer comprises detecting scattered UV wavelengths and transmitting the detected wavelength to a CCD imaging system.

7. A method of inspecting a semiconductor wafer surface according to claim 1 further comprising mapping the surface of the wafer based upon the detected radiation.

8. A method of inspecting a semiconductor wafer surface according to claim 7 wherein the step of mapping the surface of the wafer comprises transmitting the location of the scratches from the detector to a processor.

9. A method of inspecting a semiconductor wafer surface according to claim 1 wherein the step of directing radiation at a surface of the wafer comprises directing radiation at a polished surface of the wafer.

10. A method of inspecting a semiconductor wafer surface according to claim 1 wherein the step of positioning a semiconductor wafer for illumination by a radiation source and adjacent a background material comprises positioning a semiconductor wafer thick enough to absorb substantially all of the radiation having a wavelength that will be absorbed by the fundamental absorption of the wafer from the source and to substantially prevent such radiation from the source from reaching the backside of the wafer.

11. A method of inspecting a semiconductor wafer surface according to claim 1 wherein the step of positioning a semiconductor wafer for illumination by a radiation source and adjacent a background material comprises positioning a semiconductor wafer sufficiently thick to extinguish light from the source that could otherwise travel entirely through to the backside of the wafer and then be reflected to emerge from front surface of the wafer.

12. A method of inspecting a semiconductor wafer surface according to claim 1 wherein the step of positioning a semiconductor wafer for illumination by a radiation source and adjacent a background material comprises positioning a SiC wafer.

13. A method of inspecting a semiconductor wafer surface according to claim 1 wherein the step of directing radiation from the source comprises directing radiation from a source that is limited to wavelengths that will be absorbed by the fundamental absorption of the semiconductor.

14. A method of inspecting a semiconductor wafer surface according to claim 1 wherein the step of directing radiation from the source comprises directing the radiation at an angle other than normal to the wafer surface to reduce the specular back reflection as well as increase the amount of radiation scattered by scratches on the wafer surface.

15. A method of inspecting a semiconductor wafer surface according to claim 14 comprising directing the radiation at an angle of between about 20° and 40° to the surface of the wafer.

16. A method of inspecting a semiconductor wafer surface according to claim 1 wherein the step of directing radiation at a surface of a polished wafer comprises directing radiation from more than one location at the surface of the wafer.

17. A method of inspecting a semiconductor wafer surface according to claim 16 wherein the step of directing radiation from more than one location at the surface of the wafer comprises directing radiation from more than one source.

18. A method of inspecting a semiconductor wafer surface according to claim 1 wherein the step of positioning a semiconductor wafer for illumination by a radiation source and adjacent a background material that will absorb radiation from a radiation source comprises positioning the wafer in front of a background material that will absorb substantially all of the wavelengths from the radiation source.

19. A method of inspecting a surface of a polished silicon carbide semiconductor wafer for scratches, the method comprising:
  positioning a polished surface of a silicon carbide semiconductor wafer for illumination by a radiation source and adjacent a UV-absorbing material that will absorb radiation from the radiation source that is neither absorbed by the wafer nor scattered by scratches on the wafer surface;
  directing UV-radiation at the polished surface of the silicon carbide wafer from the radiation source that includes wavelengths that will be absorbed by the fundamental absorption of the silicon carbide wafer;
  filtering the UV-radiation to remove radiation having wavelengths that would not be absorbed by the fundamental absorption of the SiC wafer and to allow radiation having a wavelength that would be absorbed by the fundamental absorption of the SiC wafer to pass; and
  detecting radiation from the UV source that has been that is neither absorbed by the wafer nor scattered by scratches on the wafer surface scattered by scratches on the surface of the SiC wafer and filtered to determine the location of the scratches on the surface of the wafer.

20. A method of inspecting a surface of a double side polished silicon carbide semiconductor wafer for scratches according to claim 19 further comprising mapping the surface of the wafer after the step of detecting the radiation.

21. A method of inspecting a surface of a double side polished silicon carbide semiconductor wafer for scratches according to claim 19 wherein the step of positioning a double side polished silicon carbide semiconductor wafer for illumination by a radiation source and adjacent a UV-absorbing material comprises positioning a silicon carbide wafer thick enough to absorb substantially all of the radiation having wavelengths that will be absorbed by the fundamental absorption of the silicon carbide wafer and to prevent such radiation from reaching the backside of the wafer.

22. A method of inspecting a surface of a double side polished silicon carbide semiconductor wafer for scratches according to claim 19 wherein the step of positioning a semiconductor wafer for illumination by a radiation source and adjacent a UV-absorbing material comprises positioning a semiconductor wafer sufficiently thick to extinguish light from the source that could otherwise travel entirely through to the backside of the wafer and then be reflected to emerge from front surface of the wafer.

23. A method of inspecting a surface of a polished silicon carbide semiconductor wafer for scratches according to claim 19 wherein the step of positioning the wafer for illumination by a radiation source and adjacent a UV-absorbing material comprises positioning the wafer adjacent UV-absorbing glass.

24. A method of inspecting a surface of a polished silicon carbide semiconductor wafer for scratches according to claim 19 wherein the step of positioning the wafer for illumination by a radiation source and adjacent a UV-absorbing material comprises positioning the wafer adjacent UV-absorbing polymer.

25. A method of inspecting a surface of a double side polished silicon carbide semiconductor wafer for scratches according to claim 19 wherein the double-side polished silicon carbide semiconductor wafer is a 4H silicon carbide semiconductor wafer and the step of directing UV-radiation at a first surface of the silicon carbide wafer comprises directing radiation having a wavelength of between about 300 and 400 nm.

26. A method of inspecting a surface of a double side polished silicon carbide semiconductor wafer for scratches according to claim 19 wherein the step of filtering scattered radiation comprises allowing radiation having a wavelength of between about 330 and 360 nm to pass through a filter.

27. A method of inspecting a surface of a double side polished silicon carbide semiconductor wafer for scratches according to claim 19 wherein the step of filtering the UV-radiation to remove wavelengths comprises filtering the scratch-scattered radiation.

28. A method of inspecting a surface of a double side polished silicon carbide semiconductor wafer for scratches according to claim 19 wherein the step of filtering the UV-radiation comprises filtering the radiation from the source before it reaches the silicon carbide wafer surface.

29. A method of inspecting a surface of a double side polished silicon carbide semiconductor wafer for scratches according to claim 19 wherein the step of detecting radiation scattered by scratches on the surface of the SiC wafer and filtered comprises detecting scattered UV-wavelengths and transmitting the detected wavelength to an image capture board.

30. A method of inspecting a surface of a double side polished silicon carbide semiconductor wafer for scratches according to claim 19 wherein the step of directing UV-radiation at a first surface of the polished wafer comprises directing UV-radiation at a first surface from more than one location.

31. A method of inspecting a surface of a double side polished silicon carbide semiconductor wafer for scratches according to claim 19 wherein the step of directing UV-radiation at a first surface of the polished SiC wafer comprises directing UV-radiation at a first surface from more than one UV-radiation source.

32. A method of inspecting a surface of a double side polished silicon carbide semiconductor wafer for scratches according to claim 19 wherein the step of directing UV-radiation at a first surface of the SiC wafer comprises directing the radiation at an angle other than normal to the wafer surface to increase the amount of radiation scattered by the scratches.

33. A method of inspecting a surface of a double side polished silicon carbide semiconductor wafer for scratches according to claim 32 comprises directing UV-radiation at an angle between about 20° and 40° to the surface of the wafer.

34. An apparatus for detecting scratches on a surface of a semiconductor wafer, the apparatus comprising:
  at least one radiation source that produces radiation that includes wavelengths absorbed by the fundamental absorption of the semiconductor, said source being positioned for directing radiation at the surface of a semiconductor wafer to be inspected at an angle other than normal to the wafer surface to thereby increase the amount of radiation scattered by scratches in the wafer surface;
  a radiation detector positioned to detect source-generated and scratch-scattered radiation from the surface of the wafer;

a background material positioned relative to said source and said detector for absorbing radiation from the source that is neither absorbed by the semiconductor nor scattered by the wafer surface to thereby help prevent non-scratch scattered light from reaching the detector; and means for limiting the radiation reaching the detector to wavelengths that would be absorbed by the fundamental absorption of the semiconductor.

35. An apparatus according to claim 34 wherein said radiation-limiting means comprises at least one filter positioned relative to said wafer and said detector for absorbing radiation having wavelengths that are not absorbed by the fundamental absorption of the semiconductor while allowing radiation having wavelengths that would be absorbed by the fundamental absorption of the semiconductor to pass.

36. An apparatus for detecting scratches on a surface of a semiconductor wafer according to claim 35 wherein said filter is situated between said wafer and said detector that allows radiation having a wavelength of between about 330 and 360 nm to pass from said wafer to said detector.

37. An apparatus for detecting scratches on a surface of a semiconductor wafer according to claim 35 wherein said filter is between said radiation source and said wafer.

38. An apparatus according to claim 34 wherein said radiation-limiting means comprises a source that is limited to wavelengths that would be absorbed by the fundamental absorption of the semiconductor.

39. An apparatus for detecting scratches on a surface of a semiconductor wafer according to claim 34 further comprising a platform positioned to hold a semiconductor wafer in a proper orientation for inspection.

40. An apparatus for detecting scratches on a surface of a semiconductor wafer according to claim 39 wherein said background material is a UV-absorbing coating layer on said platform.

41. An apparatus for detecting scratches on a surface of a semiconductor wafer according to claim 39 wherein said background material is situated between said platform and the semiconductor wafer.

42. An apparatus for detecting scratches on a surface of a semiconductor wafer according to claim 39 wherein said background material is beneath a hole in said platform.

43. An apparatus for detecting scratches on a surface of a semiconductor wafer according to claim 39 further comprising means for rotating said platform to move successive wafers into position for detection.

44. An apparatus for detecting scratches on a surface of a semiconductor wafer according to claim 39 further comprising means for rotating said platform to illuminate the wafer surface from different positions relative to the position of the radiation source.

45. An apparatus for detecting scratches on a surface of a semiconductor wafer according to claim 39 wherein said platform comprises a conveyer that allows sequential analysis of more than one wafer.

46. An apparatus for detecting scratches on a surface of a semiconductor wafer according to claim 39 wherein said platform is a slide that allows the wafer to be inserted and removed from said apparatus.

47. An apparatus for detecting scratches on a surface of a semiconductor wafer according to claim 34 comprising a plurality of radiation source positions that will more completely illuminate scratches of different orientations on the surface of the wafer.

48. An apparatus for detecting scratches on a surface of a semiconductor wafer according to claim 34 comprising means for moving said radiation source to a plurality of locations sufficient to thereby illuminate and detect scratches of different orientations on the surface of the wafer.

49. An apparatus for detecting scratches on a surface of a semiconductor wafer according to claim 34 further comprising an image capture board for transferring data from said detector to digital memory.

50. An apparatus for detecting scratches on a surface of a semiconductor wafer according to claim 34 wherein said radiation source is a UV-radiation source.

51. An apparatus for detecting scratches on a surface of a semiconductor wafer according to claim 34 wherein said radiation source is a visible light source.

* * * * *